United States Patent
Acharya et al.

(10) Patent No.: US 6,195,408 B1
(45) Date of Patent: Feb. 27, 2001

(54) METHODS AND APPARATUS FOR CABLE INTERCONNECTION VERIFICATION

(75) Inventors: Kishore C. Acharya, Brookfield; James A. Blake, Franklin, both of WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/216,473

(22) Filed: Dec. 18, 1998

(51) Int. Cl.[7] .................................................. A61B 6/00
(52) U.S. Cl. ........................... 378/8; 378/95; 378/207
(58) Field of Search ........................... 378/4, 8, 95, 114, 378/204, 207

(56) References Cited

U.S. PATENT DOCUMENTS

| | | |
|---|---|---|
| 3,626,932 | 12/1971 | Becker . |
| 3,952,201 | * 4/1976 | Hounsfield ................. 378/8 |
| 4,803,639 | * 2/1989 | Steele et al. ................ 378/4 X |
| 5,751,837 | * 5/1998 | Watanabe et al. ........ 378/165 X |

FOREIGN PATENT DOCUMENTS

| | | |
|---|---|---|
| 1951232 | 4/1970 | (DE) . |
| 19503593 | 8/1996 | (DE) . |

* cited by examiner

*Primary Examiner*—David P. Porta
(74) *Attorney, Agent, or Firm*—Armstrong Teasdale LLP; Christian G. Cabou

(57) ABSTRACT

The present invention, in one form, is an imaging system which includes a verification system for verifying the proper connection of an interconnection cable. In accordance with one embodiment of the verification system, a verification circuit verifies operation of the interconnection cable by altering the patterns supplied from an EKG subsystem. More specifically, the conduction of interconnection cable is verified prior to, during and after scanning the patient by transmitting patterns received from the EKG subsystem through the verification circuit back to the EKG subsystem. If the patterns match the expected patterns, a verification signal is generated indicating proper cable connection.

16 Claims, 3 Drawing Sheets

METHODS AND APPARATUS FOR CABLE
INTERCONNECTION VERIFICATION

BACKGROUND OF THE INVENTION

This invention relates generally to computed tomography (CT) imaging and more particularly, to verification of cable interconnection in a CT imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

At least one known imaging system is used to generate images of a heart of a patient to detect coronary artery calcification (CAC). The CAC is used to identify evidence of coronary atherosclerosis in the heart. In order to identify CAC in the image data, data is collected at specific times during a cycle of the heart. One known imaging system utilizes an EKG signal from the patient to time the collection of the data. As a result, images may be generated for specific times, for example during a systolic condition, so that heart motion is minimized. To date, the EKG signal is generated using EKG electrodes which are applied to the patient and connected to the imaging system after the patient was placed on a table of the imaging system. As a result, the setup time is increased and throughput of the imaging system is negatively impacted. In addition, if the EKG signal cable is improperly connected or fails, the imaging system will be unable to generate the properly timed images. Consequently, the scan will be forced to be repeated increasing x-ray dosage to the patient.

It would be desirable to provide a system which verifies proper connection of the EKG signal before scanning of the patient. It also would be desirable that such a system detect failures of an EKG signal cable during and after scanning of the patient without significantly increasing the cost of the imaging system.

BRIEF SUMMARY OF THE INVENTION

These and other objects may be attained by an imaging system which, in one embodiment, includes a verification system having an interconnection verification unit, or circuit for verifying signal transmission of an interconnection cable. The verification circuit detects various modes of the imaging system and verifies the interconnection between an EKG subsystem and the imaging system.

In one aspect, the present invention is directed to verifying whether the interconnection cable, which couples the EKG signal generated by the EKG subsystem to the imaging system, is properly connected and conducting. The conduction of the EKG signal to the imaging system is verified prior to, during and after scanning the patient by transmitting patterns from the EKG subsystem to the imaging system. If the patterns match the expected patterns, a verification signal is generated indicating proper connection of the cable. More specifically, a signal pattern is transmitted from the EKG subsystem through the interconnection cable to the verification circuit. As a function of the scanning mode of the imaging system, the verification circuit transmits a response pattern to the EKG subsystem over the cable.

In another aspect, the present invention allows the EKG subsystem to be remotely coupled to the patient prior to the patient being placed on a table of the imaging system. More specifically, EKG electrodes may be coupled to the patient and the EKG subsystem at a site remote from the imaging system. After the patient is placed on the imaging system table, a removable interconnection cable may then be coupled to the imaging system and the EKG subsystem. The proper connection and conduction of the interconnection cable is then verified using the verification system.

The above described verification system verifies proper connection of the interconnection cable before scanning of the patient. In addition, the verification system detect failures of the cable during and after scanning of the patient without significantly increasing the cost of the imaging system. Additionally, the verification system allows the EKG subsystem to be remotely coupled to the patient to reduce setup time required to scan the patient.

DETAILED DESCRIPTION OF THE INVENTION

Figure 1:
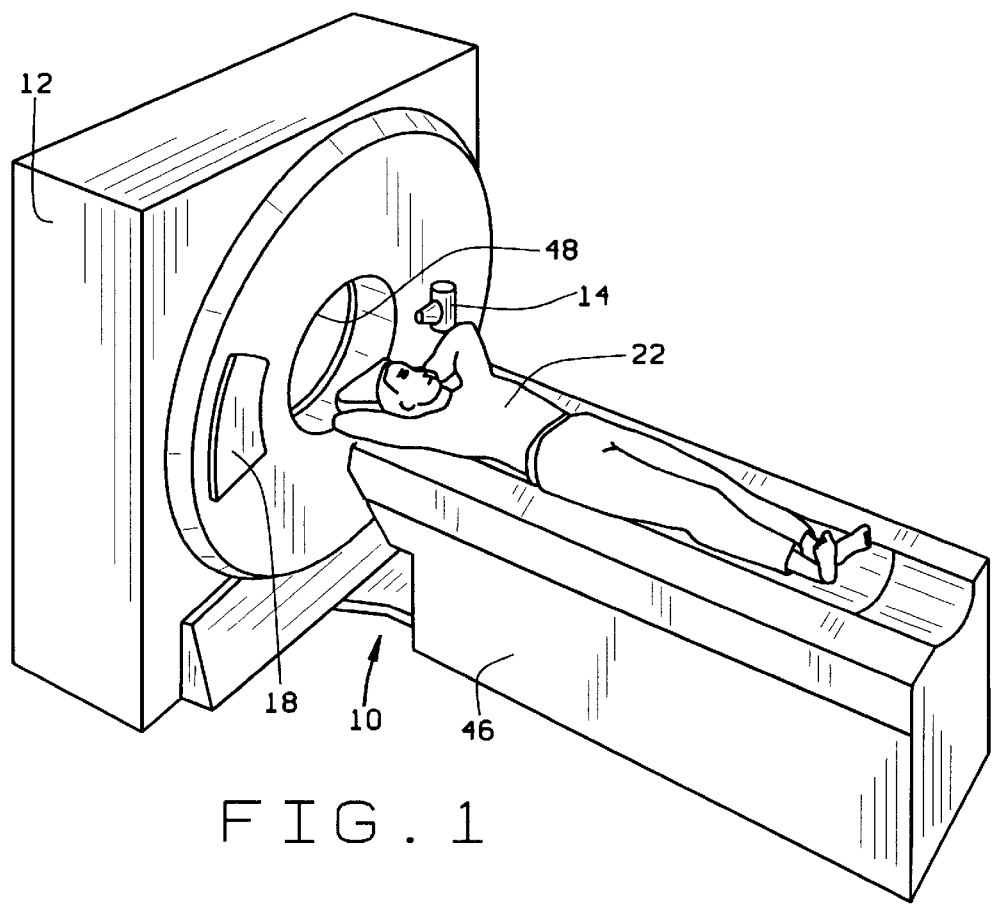
FIG. 1 is a pictorial view of a CT imaging system.
Figure 2:
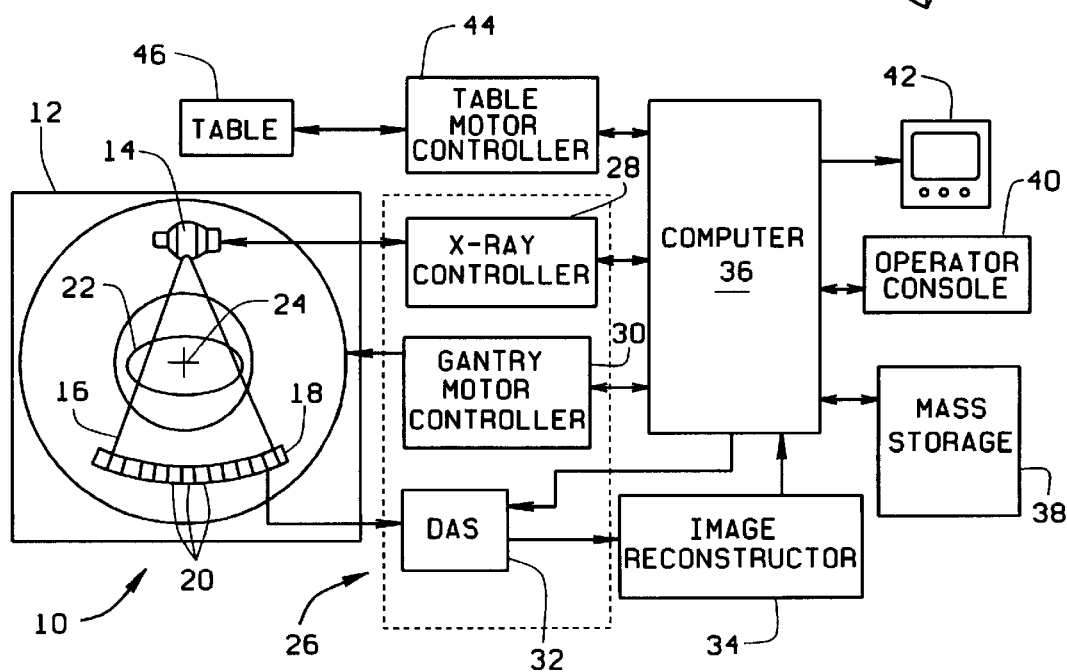
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated by a collimator (not shown) to lie within in an X-Y plane of a Cartesian coordinate system and generally referred to as an "imaging plane". Detector array 18 is formed by detector elements 20 which together sense the projected xrays that pass through a medical patient 22. Detector array 20 may be a single slice detector or a multislice detector. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
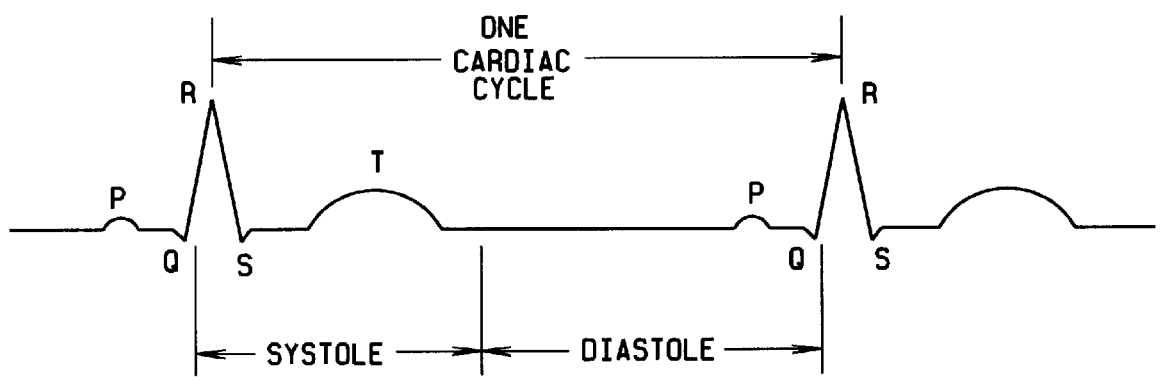
FIG. 3 is an EKG signal waveform.

In accordance with one embodiment of the present invention, system 10 is used to generate a series of images of a patient's heart, for example to assist in the detection of coronary artery calcification (CAC). In order to properly generate such images, projection data and corresponding heart data are simultaneously acquired using system 10. More specifically and in one embodiment, system 10 detects the condition, or state, of the heart of patient 22 by measuring, or determining, the state of an electrocardiography (EKG) signal generated by an EKG subsystem 100. In one embodiment, the EKG signal generated by EKG subsystem 100 represents electrical activity associated with the heart muscle versus time. Referring to FIG. 3, the EKG signal waveform illustrates one cardiac cycle including a systole condition, or period, and a diastole condition, or period of the heart. The portion of the EKG signal which is labeled Q, R and S is referred to as the QRS complex, in which the R-feature, or R-wave, is the most prominent, highest amplitude, feature of the entire EKG signal. The cardiac cycle is typically defined as beginning with a R-wave and continuing until the occurrence of the next R-wave.

In one embodiment, EKG subsystem 100 is configured to be remote from imaging system 10 so that patient 22 may be prepared outside an imaging system scanning room. More specifically, EKG electrodes (not shown) are coupled to patient and EKG subsystem 100 prior to placing patient 22 on table 46. After patient 22 is placed on table 26, EKG subsystem 100 is coupled to system 10 using a fixed or detachable interconnection cable 104. Cable 104 includes at least one conductor for transmission of the EKG signal to imaging system 10. More specifically and in one embodiment, cable 104 includes a plurality of conductors, for example electrical conductors for transmitting at least one signal between system 10 and EKG subsystem 100.

Figure 4:
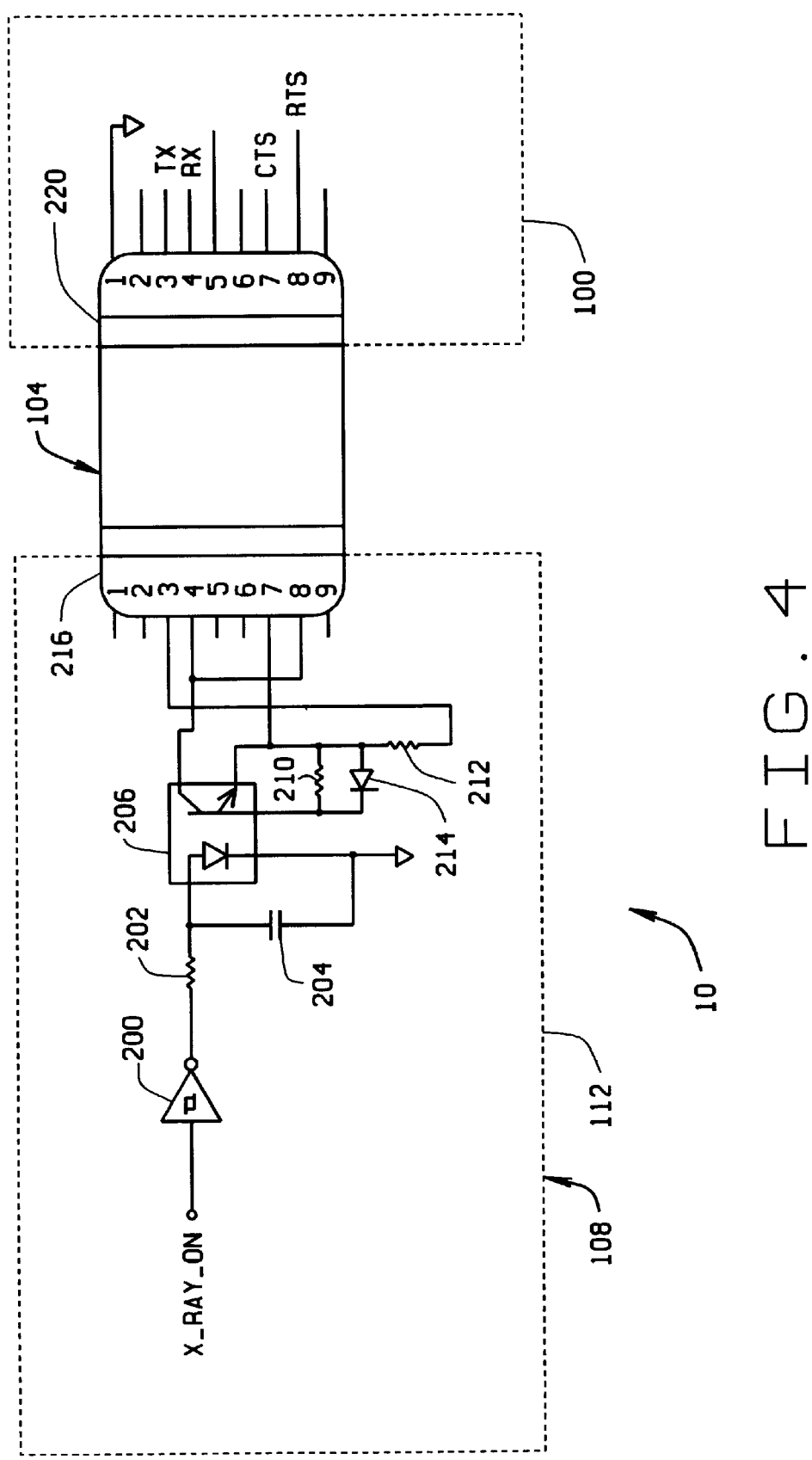
FIG. 4 is block diagram of a verification system in accordance with one embodiment of the present invention.

In one embodiment, system 10 further includes a verification system 108 for verifying the connection between imaging system 10 and EKG subsystem 100. Verification system 108 ensures that there is a proper connection, via cable 104, between system 10 and EKG subsystem 100, before, during, and after scanning object 22. More specifically and in one embodiment, verification system 108 is configured to verify signal transmission through cable 104 prior to, during, and after emission of x-ray beam 16 from source 14. As shown in FIG. 4 and in one embodiment of the present invention, verification system 108 includes an interconnection verification unit, or circuit, 112. Specifically, circuit 112 includes an inverter 200 which is configured to receive a X_RAY_ON signal from system 10, for example from computer 36. Circuit 112 also includes a first resistor 202, a first capacitor 204, an opto-isolator 206, a second resistor 210, a third resistor 212, and a diode 214. Signals are supplied between circuit 112 and cable 104 utilizing verification circuit connector 216 which is coupled to a first end of cable 104. Signals are supplied between a second end of cable 104 and EKG subsystem 100 utilizing EKG subsystem connector 220.

An output of inverter 200 is connected to a first end of first resistor 202. The junction of resistor 202 and capacitor 204 is connected to an anode of photodiode of opto-isolator 206. A junction of a cathode of photodiode of opto-isolator 206 and capacitor 204 is connected to ground. A junction of pins 4 and 8 of connector 216 is connected to a collector of opto-isolator 206. The junction of resistor 210 and a cathode of diode 214 is connected to a base input of opto-isolator 206. Pin 7 of connector 216 is connected to a junction of an emitter of opto-isolator 206, resistor 210, an anode of diode 214, and resistor 212. Resistor 212 is connected to pin 3 of connector 216. In one embodiment of EKG subsystem 100, an EKG_Gnd signal is connected to pin 1 of connector 220. A TX signal is connected to pin 3 of connector 220. A RX signal is connected to pin 4 of connector 220. A CTS signal is connected to pin 7 and a RTS signal is connected to pin 8 of connector 220.

Circuit 112 has two different modes, or states of operation. These states of operation are referred to herein as the non-scanning mode and the scanning mode. The non-scanning mode of circuit 112 refers to that state of circuit 112 when system 10 is not emitting x-ray beam 16 from source 14. In the non-scanning mode, the X_RAY_ON signal supplied to circuit 112 from system 10, for example from computer 36, is a first level, for example approximately zero volts. Consequently, the voltage applied to resistor 202 and capacitor 204 enables, or turns on, opto-coupler 206 so that the signal applied to pin 7 of connector 216 is supplied to pin 8 of connector 216.

The scanning mode of circuit 112 refers to that state of circuit 112 when system 10 is emitting x-ray beam 16 from source 14. In the scanning mode, the X_RAYON signal supplied from system 10 is a second level, for example a positive voltage greater than 3 volts. Consequently, opto-isolator 206 is turned off and the signal supplied to pin 8 of connector 216 is no longer connected to pin 7 of connector 216. In addition, the level of the signal at pin 7 of connector 216 transitions to a second state, for example a negative voltage, if a second state signal is supplied to pin 3 of connector 216 through resistor 212.

In operation, after coupling at least one EKG electrode to patient 22 and EKG subsystem 100, cable 104 is coupled between EKG subsystem 100 and system 10, for example computer 36. Prior to scanning, i.e., X_RAY_ON signal is set to a first state, signal transmission is verified by transmitting a first pattern through interconnection cable 104. More specifically, a first state, for example a positive voltage, RTS signal is supplied from EKG subsystem 100 to pin 8 of connector 220. In addition, a second state TX signal, for example a negative voltage, is supplied to pin 3 of connector 220. If cable 104 is properly connected and conducting the signals, the RTS first state signal supplied to pin 8 of connector 216 is coupled through circuit 112 to pin 4 of connector 216. As a result, the RX signal supplied to EKG subsystem 100 equals the state of the RTS signal supplied from EKG subsystem 100. In addition, the first state RTS signal supplied from EKG subsystem 100 is coupled through opto-coupler 206 to pin 7 of connector 216 which is supplied to pin 7 of connector 220, if cable 104 is properly connected and conducting the signals. By verifying that the state of the RX and CTS signals supplied to EKG subsystem 100, the operation and conduction of cable 104 is verified. More specifically, in the non-scanning mode, the operation of cable 104 is verified if both the state of the CTS signal and the state of the RX signal equal the state of the RTS signal supplied from EKG subsystem 100. If the state of both the CTS and RX signals are equal to the state of the RTS signal, a first state cable verification signal is generated, for example a positive voltage, indicating proper conduction. In one embodiment the first state verification signal may be used to illuminate a "good connection" indicator. If the state of either the CTS signal or the RX signal is not equal to the state of the RTS signal, the cable verification signal is set to a second state, for example zero volts, so that an alarm or failure indication is set. For example, if the cable verification signal is equal to a second state, a failure indicator is illuminated or activated.

During a scan, i.e., when X_RAY_ON is set to a second state, in addition to collecting projection data and transmitting the EKG signal from EKG subsystem 100 to system 10 using cable 104, signal transmission is verified by transmitting a second pattern through interconnection cable 104. More specifically, the second state of X_RAY_ON transitions opto-coupler 206 to an off state so that the first state RTS signal supplied from EKG subsystem 100 on pin 8 of connector 220 is prevented from being coupled through circuit 112 to pin 4 of connector 216. Therefore, the second state TX signal supplied to pin 3 of connector 220 is coupled through cable 104 through resistor 212 and supplied to pin 7 of connector 216. As a result, the second state TX signal is supplied through cable 104 to supply a second state CTS signal to pin 7 of connector 220 of EKG subsystem 100 if the cable 104 is properly connected and conducting the signals. In addition, the first state RTS signal supplied from EKG subsystem 100 is coupled through circuit 112 and cable 104 to pin 4 of connector 216 which is supplied to pin 4 of connector 220 if cable 104 is properly connected and conducting the signals. By verifying the levels of the RX and CTS signals supplied to EKG subsystem 100, the operation and conduction of cable 104 is verified. More specifically, in the scanning mode, the operation of cable 104 is verified if the state of the CTS signal equals the state of the TX signal and the state of the RX signal equals the state of the RTS signal supplied from EKG subsystem 100. If the state of both the CTS and RX signals are correct, a first state cable verification signal is generated, for example to illuminate a "good conduction" indicator. If the state of either the CTS signal is not equal to the state of the TX signal or the RX signal is not equal to the state of the RTS signal, the cable verification signal is set to a second state and as described above an alarm or failure indication may be set.

After completion of the scanning, X_RAY_ON signal is again set to a first state, and signal transmission is verified through interconnection cable 104 as described above for the prior to scanning mode. Specifically, operation of cable 104 is verified if both the state of the CTS signal and the state of the RX signal equal the state of the RTS signal supplied from EKG subsystem 100.

The above described verification system verifies proper connection of the interconnection before scanning of the patient. In addition, the verification system detect failures of the cable during and after scanning of the patient without significantly increasing the cost of the imaging system. Additionally, the verification system allows the EKG subsystem to be remotely coupled to the patient to reduce setup time required to scan the patient.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for verifying connection of an interconnection cable having a first end, a second end, and a plurality of conductors therebetween, to a subsystem and to an imaging system having a detector, an x-ray source operable to emit an x-ray beam toward the detector, and an optically isolated verification circuit, said method comprising the steps of:
   interconnecting the first end of the interconnection cable to the subsystem;
   interconnecting the second end of the interconnection cable to the verification circuit;
   transmitting a signal from the subsystem to the verification circuit;
   returning the transmitted signal to the subsystem via a set of conductors of the interconnection cable, the set of conductors being dependent upon a state of operation of the x-ray source; and
   optically isolating the returned signals from the imaging system.

2. A method in accordance with claim 1 wherein verifying signal transmission through the interconnection cable comprises the steps of verifying signal transmission of the interconnection cable prior to emitting the x-ray beam.

3. A method in accordance with claim 2 wherein verifying signal transmission of the interconnection cable further comprises the steps of verifying signal transmission of the interconnection cable during emission of the x-ray beam.

4. A method in accordance with claim 3 wherein verifying signal transmission of the interconnection cable prior to emitting the x-ray beam comprises the step of verifying transmission of a first signal pattern using the interconnection cable.

5. A method in accordance with claim 4 wherein verifying signal transmission of the interconnection cable during emission of the x-ray beam comprises the steps of verifying transmission of a second signal pattern using the interconnection cable.

6. A method in accordance with claim 1 further comprising the step of transmitting an analog waveform from the subsystem to the imaging system through the interconnection cable while the x-ray beam is being emitted.

7. A method in accordance with claim 1 wherein the subsystem is an EKG subsystem, the EKG subsystem is configured to generate an EKG signal, and wherein the interconnection cable is configured to supply the EKG signal from the EKG subsystem to the imaging system, said method further comprising the step of transmitting the EKG signal through the interconnection cable.

8. A method in accordance with claim 7 further comprising the step of transmitting an analog EKG waveform from the EKG subsystem to the imaging system through the interconnection cable while the x-ray beam is being emitted.

9. An imaging system for generating images of an object, said imaging system comprising a subsystem, an optically isolated verification circuit, and an interconnection cable having a first end, a second end, and a plurality of conductors therebetween, said imaging system further including a detector and an x-ray source operable to emit an x-ray beam toward said detector, said optically isolated verification circuit having an opto-isolator configured to switch a state of said verification system dependent upon the emission of the x-ray beam, and said verification system configured to:

verify signal transmission through said interconnection cable prior to emitting the x-ray beam and to continuously verify signal transmission while the x-ray source emits the x-ray beam.

10. An imaging system in accordance with claim 9 wherein to verify signal transmission of said interconnection cable prior to emitting the x-ray beam, said circuit is configured in a first state to verify transmission of a first signal pattern using said interconnection cable.

11. An imaging system in accordance with claim 9 wherein to verify signal transmission of said interconnection cable during emission of the x-ray beam, said circuit is configured in a second state to verify transmission of a second signal pattern using said interconnection cable.

12. An imaging system in accordance with claim 9 wherein said subsystem is configured to transmit an analog signal through said interconnection cable during emission of the x-ray beam.

13. An imaging system in accordance with claim 12 wherein said subsystem is an EKG subsystem, and said analog signal is an EKG signal.

14. A verification system for verifying connection of an interconnection cable having a first end, a second end, and a plurality of conductors therebetween, to a subsystem and to an imaging system having a detector, an x-ray source operable to emit an x-ray beam towards the detector, and an optically isolated verification circuit, said verification system having an opto-isolator configured to switch a state of the verification system dependent upon the emission of the x-ray beam, and said verification system configured to:

verify signal transmission through said interconnection cable.

15. A verification system in accordance with claim 14 wherein to verify signal transmission of the interconnection cable prior to emitting the x-ray beam, said verification system is configured in a first state to verify transmission of a first signal pattern using the interconnection cable.

16. A verification system in accordance with claim 15 wherein to verify signal transmission of the interconnection cable during emission of the x-ray beam, said verification system is configured in a second state to verify transmission of a second signal pattern using the interconnection cable.

* * * * *

UNITED STATES PATENT AND TRADEMARK OFFICE
CERTIFICATE OF CORRECTION

PATENT NO. : 6,195,408 B1
APPLICATION NO. : 09/216473
DATED : February 27, 2001
INVENTOR(S) : Acharya et al.

It is certified that error appears in the above-identified patent and that said Letters Patent is hereby corrected as shown below:

In Claim 11, column 8, line 3, please delete "9" and substitute -- 10 --.

Signed and Sealed this

Seventh Day of November, 2006

JON W. DUDAS
*Director of the United States Patent and Trademark Office*